United States Patent [19]

Lennox

[11] Patent Number: 5,782,848
[45] Date of Patent: Jul. 21, 1998

[54] RESECTING COAGULATED TISSUE

[75] Inventor: Charles D. Lennox, Hudson, N.H.

[73] Assignee: Boston Scientific Corporation, Natick, Mass.

[21] Appl. No.: 707,060

[22] Filed: Sep. 3, 1996

Related U.S. Application Data

[63] Continuation of Ser. No. 235,177, Apr. 29, 1994, abandoned.

[51] Int. Cl.[6] .................................................. A61B 17/22
[52] U.S. Cl. .......................... 606/159; 128/756; 606/170; 604/22
[58] Field of Search .................................. 606/159, 170, 606/171, 180, 160, 161, 162; 604/22; 128/756

[56] References Cited

U.S. PATENT DOCUMENTS

| | | | |
|---|---|---|---|
| 2,955,591 | 10/1960 | MacLean | 128/756 |
| 4,560,373 | 12/1985 | Sugino et al. | |
| 4,899,741 | 2/1990 | Bentley et al. | 606/27 |
| 4,946,440 | 8/1990 | Hall | 604/95 |
| 4,955,882 | 9/1990 | Hakky | 606/14 |
| 5,030,090 | 7/1991 | Maeda et al. | 433/29 |
| 5,045,061 | 9/1991 | Seifert et al. | 604/96 |
| 5,056,529 | 10/1991 | de Groot | 128/754 |
| 5,059,200 | 10/1991 | Tulip | 606/128 |
| 5,061,266 | 10/1991 | Hakky | 606/15 |
| 5,074,862 | 12/1991 | Rausis | 606/19 |
| 5,116,615 | 5/1992 | Gokeen et al | 424/94.2 |
| 5,176,677 | 1/1993 | Wuchinich | 606/46 |
| 5,201,731 | 4/1993 | Hakky | 606/15 |
| 5,207,672 | 5/1993 | Roth et al. | 606/10 |
| 5,341,816 | 8/1994 | Allen | 606/180 |
| 5,427,115 | 6/1995 | Rowland et al. | |
| 5,454,807 | 10/1995 | Lennox et al. | 606/15 |

OTHER PUBLICATIONS

Crispin, H. and Verhulst, A.; "Use of the Vascular Brush in Angioscopically–Assisted Endarterectomy"; International Congress VII: Endovascular Interventions (On the Cutting Edge); Feb., 1994.

Primary Examiner—Michael Buiz
Assistant Examiner—Daphna Shai
Attorney, Agent, or Firm—Fish & Richardson P.C.

[57] ABSTRACT

The invention relates to quickly and efficiently removing coagulated tissue within a body lumen without affecting the normal, healthy, untreated tissue, to minimize post-operative complications such as bleeding or edema formation. For example, in an aspect, the invention features a surgical resecting brush assembly. The assembly includes an elongated catheter sized and constructed for delivery through an extended body lumen to a site that is occluded with body matter that has been effected by heat treatment and a brush formation near the distal end of the catheter. The brush formation includes a bristle structure of sufficient stiffness to resect and remove the effected bodily matter without substantially damaging adjacent healthy tissue when the brush formation is actuated relative to the occluded site.

27 Claims, 7 Drawing Sheets

RESECTING COAGULATED TISSUE

This is a continuation of application Ser. No. 08/235,177, filed Apr. 29, 1994, now abandoned.

FIELD OF THE INVENTION

This invention relates to resecting tissue.

BACKGROUND OF THE INVENTION

Various surgical instruments and surgical procedures have been developed for removing obstructive tissue from body lumens. For example, obstructive tissue may be removed by a cutting element, such as, for example, a blade. Traditional cutting elements are not able to distinguish between the obstructive tissue causing the problem and healthy tissue. Additionally, these procedures can be time-consuming and can generate significant blood loss. For example, in the treatment of benign prostate hyperplasia, a technique known as Transurethral Resection of the Prostate (TURP), removes obstructing tissue by dragging a cutting wire, energized by radio frequency energy, along the urethra, carving out small sections of tissue as it is moved. Besides bleeding, other possible complications that can occur include retrograded ejaculation, urinary incontinency and impotence.

Laser radiation has also been used to treat obstructed tissue in body lumens such as, for example, in the prostate. In this case, the tissue is coagulated when it absorbs the laser light. Over time, after the laser treatment, the treated tissue is removed either by bodily absorption or by sloughing, where the coagulated tissue separates from the normal tissue and is carried away from the site and excreted. A complication that can arise in this treatment is that, when a large volume of tissue is coagulated within a lumen, edema can develop, which causes a narrowing of the lumen due to the accumulation of fluid at the periphery of the coagulated zone. A urinary bypass catheter is placed through the prostate to allow urine to flow, but the catheter prevents the tissue from being sloughed from the lumen wall.

SUMMARY OF THE INVENTION

The invention relates to quickly and efficiently removing coagulated tissue within a body lumen without affecting the normal, healthy, untreated tissue, to minimize post-operative complications such as bleeding or edema formation.

In a first aspect, the invention features a surgical resecting brush assembly. The assembly includes an elongated catheter sized and constructed for delivery through a body lumen to a site that is occluded with body matter that has been effected by heat treatment, and a brush formation near the distal end of the catheter. The brush formation includes a bristle structure of sufficient stiffness to resect and remove the effected bodily matter without substantially damaging adjacent healthy tissue when the brush formation is actuated relative to the occluded site.

In another aspect, the invention features a surgical kit for treating occluded body lumens. The kit includes a tissue coagulating implement for coagulating bodily matter at a selected site and a selective resecting surgical instrument, constructed with an elongated instrument body for delivery through the working channel. The selective resecting surgical instrument enables resection and removal of coagulated bodily matter at the site without substantial damage to adjacent healthy bodily matter.

In another aspect, the invention features a selective resecting surgical instrument. The instrument has an elongated instrument body constructed for delivery through an extended body lumen to a site that is occluded with body matter that has been coagulated and a resecting formation to resect and remove the coagulated bodily matter without substantially damaging adjacent healthy tissue.

Embodiments may include one or more of the following. The brush assembly includes an atraumatic guiding tip positioned distally of the bristle structure. The catheter includes torque-transmission structure so that the brush at the distal end of the catheter can be rotated by torque application at the proximal end of the catheter. The catheter includes an axial stiffner so that the catheter can be delivered through the pathway by application of axially compressive forces to the proximal end of the catheter. The catheter includes a biocompatible polymeric outer coating. The brush formation includes bristle structure having a stiffness of about $1500N/mm^2$. The bristles extend radially from the catheter. The diameter of the brush formation corresponds, substantially, to the diameter of the lumen in a healthy, non-occluded condition. The length of the brush formation corresponds substantially to the length of the occluded site. The brush assembly includes coupling structure for coupling the assembly to a delivery catheter. The brush assembly includes a crank assembly constructed for use with the coupling structure for actuating the brush from outside the body while the brush assembly is positioned through the catheter inside the body. The crank assembly and coupling structure are connected through a swivel coupling. The catheter is releasably connected to the coupling structure or crank assembly by a compression fitting. The catheter is an endoscope or a cystoscope. The kit includes a tissue coagulating implement constructed for delivery through the working channel to effect bodily matter of the site. The resecting formation is a water jet nozzle.

In another aspect, the invention features a method for treating an occluded body lumen by advancing a tissue coagulating implement into the body lumen, positioning the coagulating implement at the occluded site to cause coagulation of bodily matter at the site, advancing a selective resecting brush into the body lumen, the resecting brush having an elongated catheter and a brush formation, the brush formation located near the distal end of the catheter, positioning the brush formation at the occluded site and actuating the brush formation to resect and remove the coagulated bodily matter without substantially damaging adjacent healthy tissue, and removing the coagulating implement, and the resecting brush from the patient.

In embodiments, the method may also include one or more of the following. The method may include inserting a delivery catheter into the body lumen and inserting the tissue coagulating implement and resecting brush through the catheter. The method may include treating the prostate for benign prostate hyperplasia. The method may include using a coagulating implement that is a heating implement such as a laser transmission apparatus. The method may include flushing the body lumen during the resecting treatment of the body lumen. The method may include resecting the tissue by rotating the surgical brush formation. The method may also include the steps of using the elements discussed above with respect to the resecting brush, the surgical kit, and the resecting surgical instrument.

Other aspects, features, and advantages follow.

DESCRIPTION OF THE PREFERRED EMBODIMENTS

Structure

Figures 1, 1A:
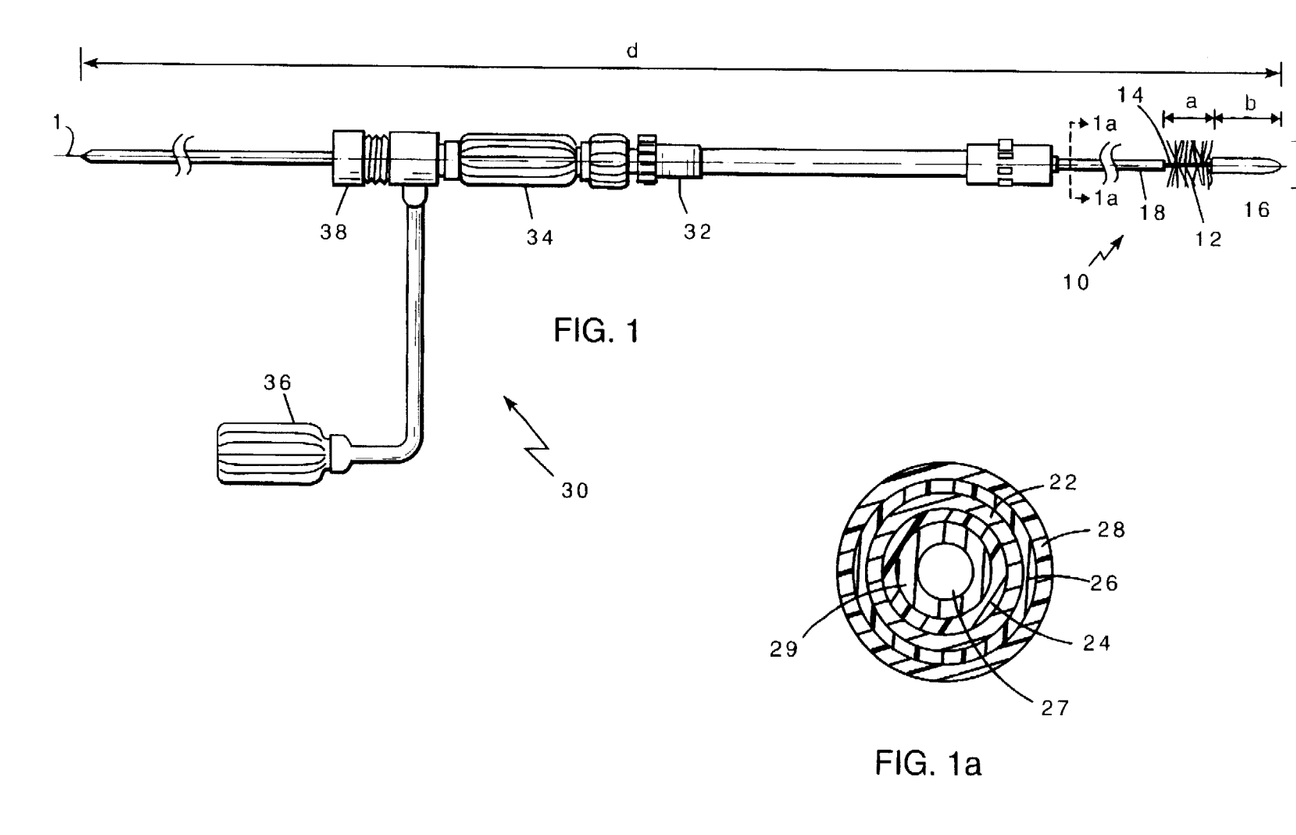
FIG. 1 is a side view of a resecting assembly.
FIG. 1a is an enlarged cross-sectional view of the torque catheter of the resecting brush taken along line 1a—1a of FIG. 1.

Referring to FIG. 1, an assembly, suitable for removing obstructive tissue from a body lumen following thermal coagulation of the body tissue by, for example, laser irradiation, includes an actuation assembly 30 constructed for use with a resecting brush 10 that includes bristles 12, bristle support shaft 14, atraumatic guiding tip 16, and torque catheter or elongated catheter 18. The support shaft 14 is formed from at least two wires twisted about bristles 12 such that the bristles extend radially outward from and 360° around support shaft 14. The brush is constructed so that it can remove a desired tissue-type without removing or damaging another tissue-type that is near to the desired type. This function is dependent upon the force applied to the tissue by the brush, which depends on the brush stiffness, which is dependent on bristle stiffness and bristle length from the supporting shaft, and on the force with which the bristles engage the tissue, which is in turn dependent on actuation speed. These parameters are dependent upon the body lumen, and the type of obstructive tissue to be removed from the body lumen.

In a preferred embodiment, brush 10 is used to remove tissue coagulated after laser irradiation in the prostate to treat, for example, benign prostatic hyperplasia. Actuation of brush 10 causes bristles 12 to remove tissue that has been affected by heat treatment, without affecting the normal, healthy, untreated tissue that is adjacent (axially or radially) to the treated tissue. The bristles 12 have an axial length "a" of about 1 cm and diameter "c" of about 0.5 cm to about 1 cm, which corresponds to the length and width of a healthy prostate. The diameter of each bristle is about 0.004 in. and preferably formed from a polymer, such as, for example, nylon 12, with a durometer of about 75 Shore hardness. Alternatively, the bristles may be formed from a metal such as stainless steel, for example, having a bristle diameter of about 0.0005 in. to about 0.001 in.

Support shaft 14 extends distally from the distal end of bristles 12 through length "b" to form atraumatic tip 16. The tip is formed by molding a piece of nylon, for example, about support shaft 14 to form a blunt, flexible, atraumatic tip 16 that is used to guide the resecting brush 10 through a cystoscope and through the collapsed urethra during use. The length "b" of tip 16 is about 1 cm. The proximal end of support shaft 14 is attached to torque catheter 18, as will be described further below. The overall length "d" of the torque catheter 18, including bristles 12 and tip 16, is about two feet, and is dependent upon the length of a cystoscope or delivery catheter 40, (see FIG. 2) actuation assembly 30, and the axial distance brush 10 moves in order to resect the treated tissue in a particular embodiment.

Referring particularly to FIG. 1a., the torque catheter 18 has an overall diameter 2.3 mm and is constructed by sandwiching a layer of stainless steel mesh 22 between an inner and outer layer 24, 26, of a polymer, such as nylon, to form a tubular torque catheter shaft with an inner lumen 27. The outer polymer layer 26 is laminated 28 with a polymer that is biocompatible, such as nylon. Disposed within the lumen is a wire coil 29 which imparts compressive strength and kink resistance to torque catheter 18 and enables the torque catheter 18 to withstand axial compression and transmit a torque through the length of the torque catheter 18. Wire coil 29 is typically formed from a biocompatible stainless steel coil. The support shaft 14 extends proximally into the catheter about 5.0 cm and is attached to the coil by, for example, welding. (The support shaft 14 and the wire coil may additionally be glued and pinned.) This construction enables the torque catheter 18 to translate torque applied at its proximal end to the distal end such that rotation at the proximal end of torque catheter 18 causes similar rotation of the bristles 12.

Figure 2:
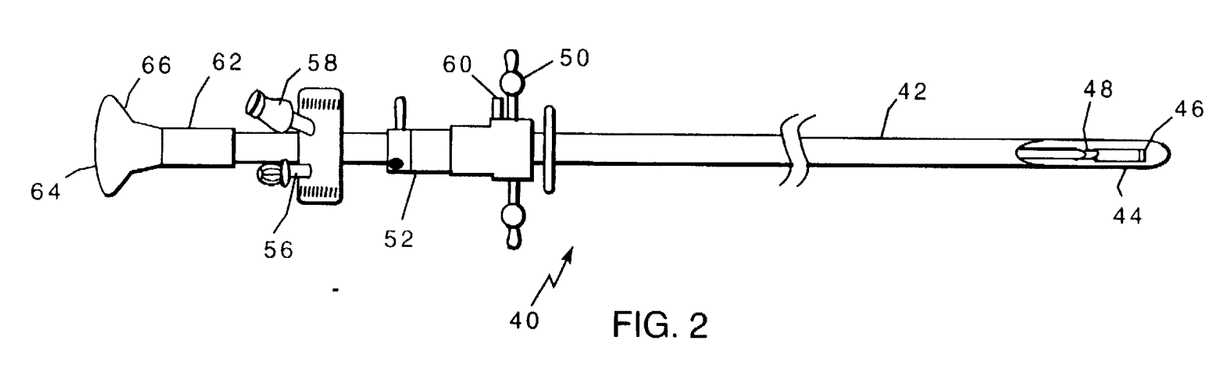
FIG. 2 is a top view of a cystoscope.

Referring back to FIG. 1, torque is applied to resecting brush 10, through the torque catheter 18, by actuation assembly 30 that is constructed for use with a cystoscope 40 (see FIG. 2). Actuation assembly 30 includes connector 32, swivel fitting 34, crank handle 36, and tuohy-borst connector 38. Connector 32 fastens actuation assembly 30 onto cystoscope 40, as will be discussed in more detail below. Swivel fitting 34 enables relative motion between actuation assembly 30 and cystoscope 40 when a physician rotates crank handle 36 about centerline 1 of actuation assembly 30. Tuohy-borst connector 38 is tightened about torque catheter 18 such that when crank handle 36 is rotated about centerline 1 of crank assembly 30, swivel fitting 34 and tuohy-borst connector 38 similarly rotate such that a torque is applied to the torque catheter 18 which translates to rotation of bristles 12.

Referring to FIG. 2, the resecting brush 10 and actuation assembly 30 are used with a standard cystoscope 40, (e.g. Karl Storz, model number 27026B, Germany). Cystoscope 40 may also be used for the laser procedure, which typically precedes the use of the resecting brush 10 and crank assembly 30, as will be discussed further below. Cystoscope 40 includes a sheath 42, bridge 52 and telescope 62. Sheath 42 defines two axially extending working channels (diameter about 3.3 mm) and has ovular opening 44 at the distal end such that the telescope lens 46, at the distal end of telescope 62, has a field of view and such that a deflection arm 48, which allows for the manipulation of a surgical instrument, such as a laser fiber or a resecting brush 10, can be deflected at the distal end of sheath 42. Deflecting handles 50 are used by the physician to manipulate deflection arm 48. The bridge 52 is secured into sheath 42 by a bayonet connection with a rotating lock joint (not shown). Bridge 52 has access ports 56 and 58 to the working channels of sheath 42. The bridge 52 also includes an irrigation port 60 through which irrigation fluid such as saline can be delivered to flow out the opening 44. Telescope 62 is mounted onto bridge 52 by a bayonet connection (not shown). The distal end 46 of telescope 62 ends just proximal the distal end of sheath 42. The proximal end 64 of telescope 62 has an eyepiece 66. Alternatively, a video system (not shown) may be attached to eyepiece 66 so that the physician may view the procedure on video monitors.

Figure 3:
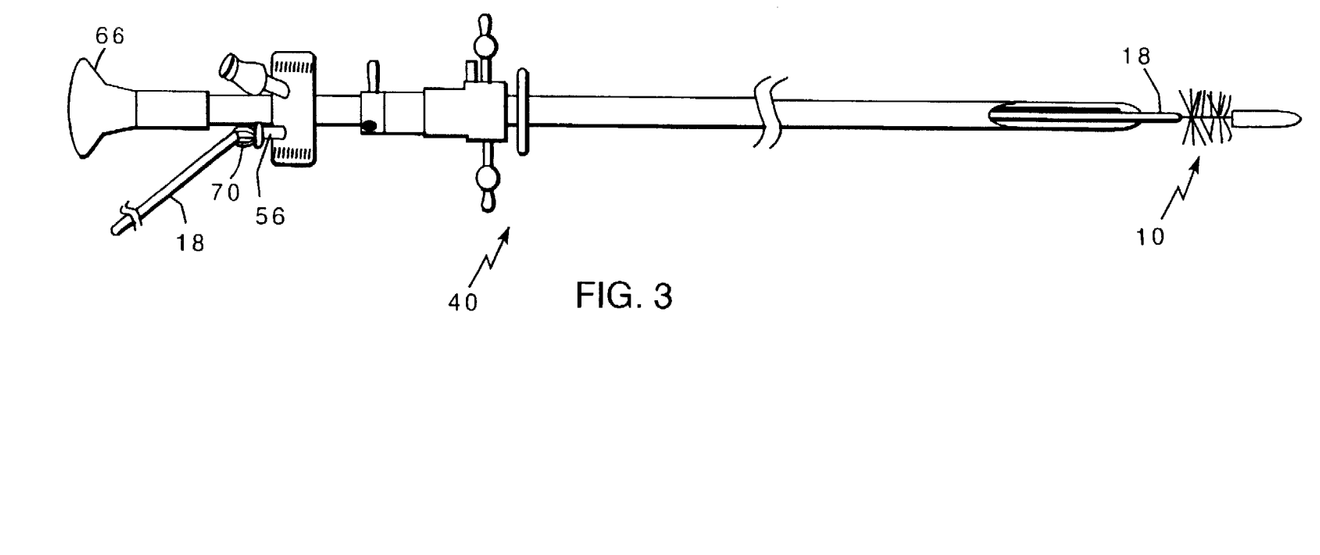
FIG. 3 is a top view of a cystoscope of FIG. 2 with a resecting brush inserted into its working channel.
Figure 4:
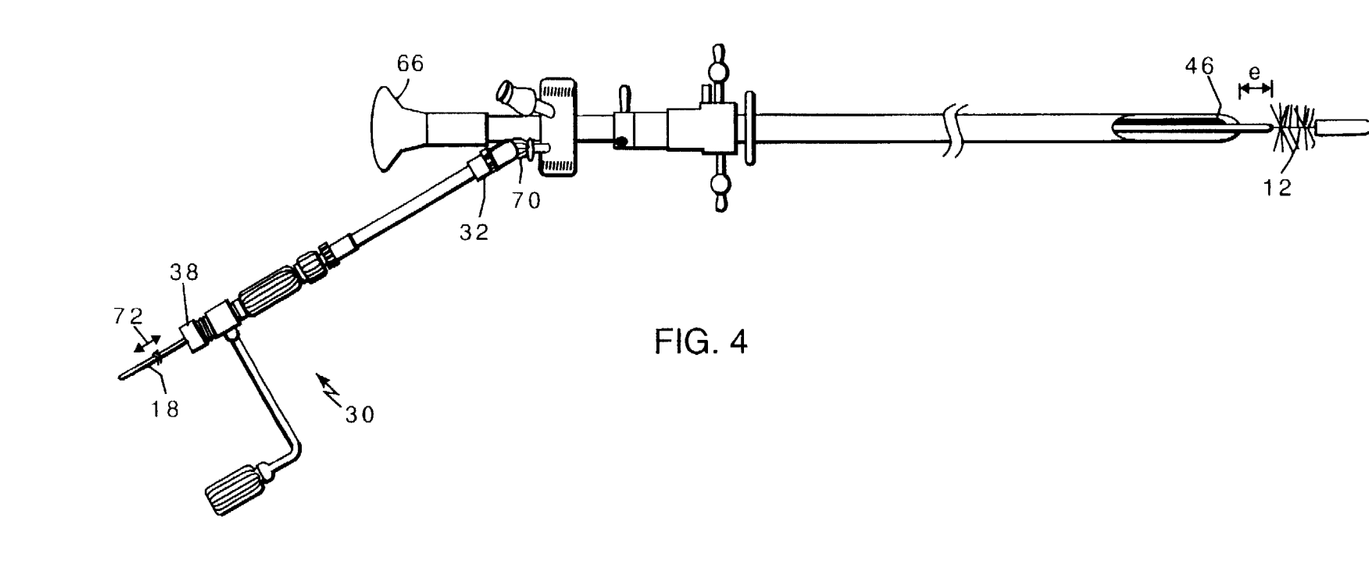
FIG. 4 is a top view of the resecting assembly mounted on a cystoscope, with the proximal end of the resecting brush inserted through a crank assembly.

Referring to FIG. 3, to assemble the system for resection, resecting brush 10 is slid through port 56, which has a fitting such as, for example, a ball fitting 70, and into one of the working channels. Referring to FIG. 4, actuation assembly 30 is then placed over the proximal end of torque catheter 18. The tuohy-borst connector 38 is loosened so that it is in the open position. Actuation assembly 30 is attached to cystoscope 40 by fastening connector 32 at the end of the swivel connector to ball fitting 70. The proximal end of torque catheter 18 is then manipulated in the direction of arrow 72 until the proximal end of bristles 12 is located a distance "e" from the distal end of sheath 42. Preferably, distance "e" is about 1 cm so the bristles 12 of the resecting brush 10 stay relatively close to lens 46 and within the physician's view. When the bristles 12 are located in the desired position, tuohy-borst connector 38 is tightened about torque catheter shaft 18. In this condition, rotation of the crank assembly 30 translates into rotation of the torque catheter 18 and brush 12.

Use

Figure 5:
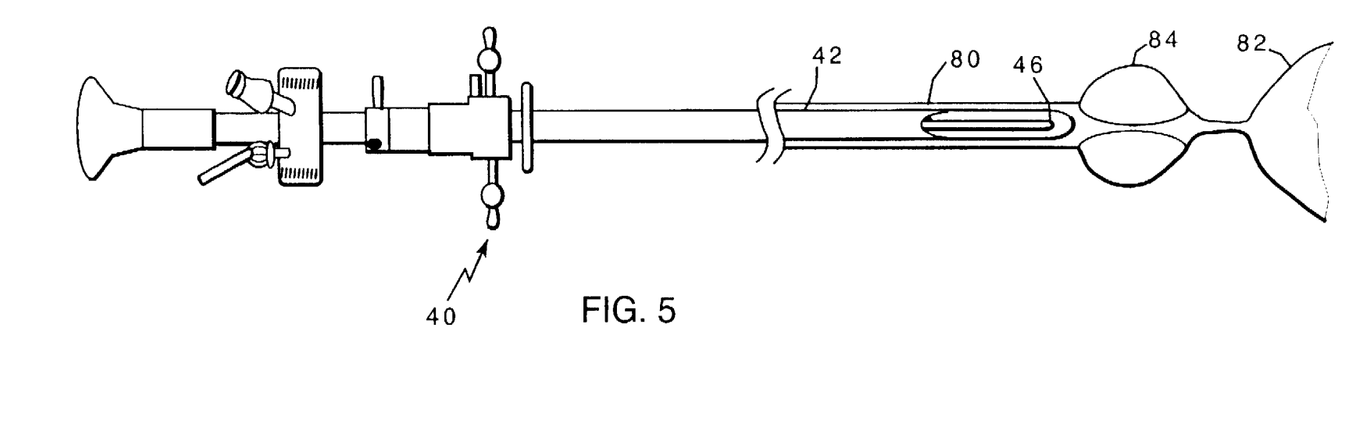
FIGS. 5 to 5e illustrate a use of a resecting assembly in treating benign prostatic hyperplasia.

The following method can be used to treat benign prostatic hyperplasia. Referring to FIG. 5, a physician inserts sheath 42 of cystoscope 40 into urethra 80. The urethra is a lumen that is usually closed by prolapse of the lumen walls and opens only when pressure is applied by urine from the bladder. Sheath 42 of cystoscope 40 partially opens the urethra and enables the physician to perform a visual examination of the prostate 84 using telescope lens 46 and also to measure the length of prostate 84 and to determine the strategy for the procedure and the laser dosage to be used. (Additionally, as part of the cystoscopic examination, the doctor will locate the bladder and sphincter (not shown) and examine the bladder for cancer).

Figure 5A:
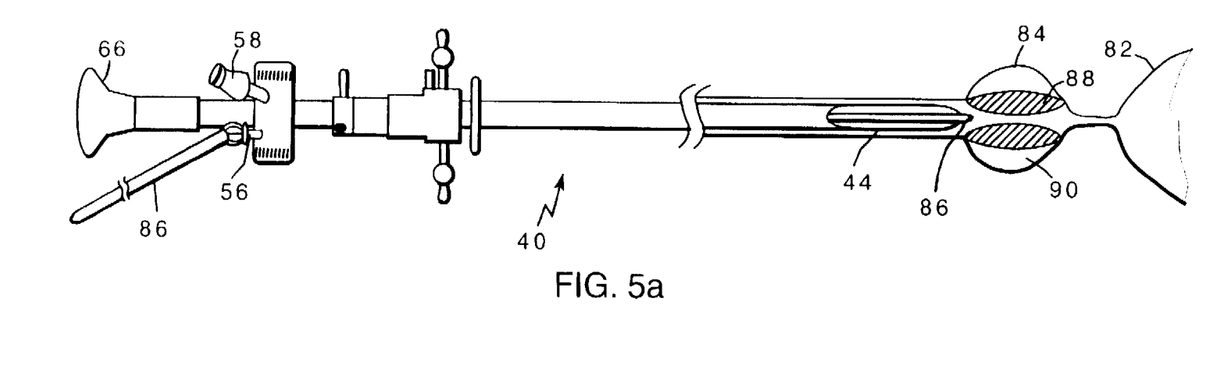

Referring to FIG. 5a, when the cystoscopic examination is complete, a laser fiber 86 is advanced through one of the working channels, accessed through ports 56, 58 of cystoscope 40 and through ovular opening 44 into prostate 84. Laser fiber 86 is attached to a laser system (not shown) which provides a visible aiming beam, used to direct the treatment laser, and a treatment laser, preferably a Nd-YAG laser. The physician then mentally divides the prostate into four quadrants, each quadrant corresponding to the 2, 4, 8 and 10 o'clock positions respectively. Each quadrant is lased at 60 watts for approximately one minute. This results in a circumferential laser coagulated adenoma 88, which is about 1 cm deep and axially about 1 cm long, in the prostatic tissue. A ring of blood and edema (not shown) may form about coagulated adenoma 88, which is then surrounded by normal tissue 90. The laser treatment affects the nature of the irradiated tissue in that the extra cellular matrix of crosslinked collagen that holds cells together is generally destroyed by necrosis. The cells also shrink and dehydrate. The tissue takes on a granular consistency in which adjacent cells are not securely connected. Generally, one polar coordinate treatment, in each quadrant, is sufficient. However, in larger prostates, the laser fiber 86 may be moved axially, about 1 cm to 2 cm, in order to lase each quadrant again at the new axial location. A suitable system for use with an endoscope is described in U.S. Ser. No. 08/062,656, filed May 14, 1993, the contents of which is incorporated herein by reference.

Figure 5B:
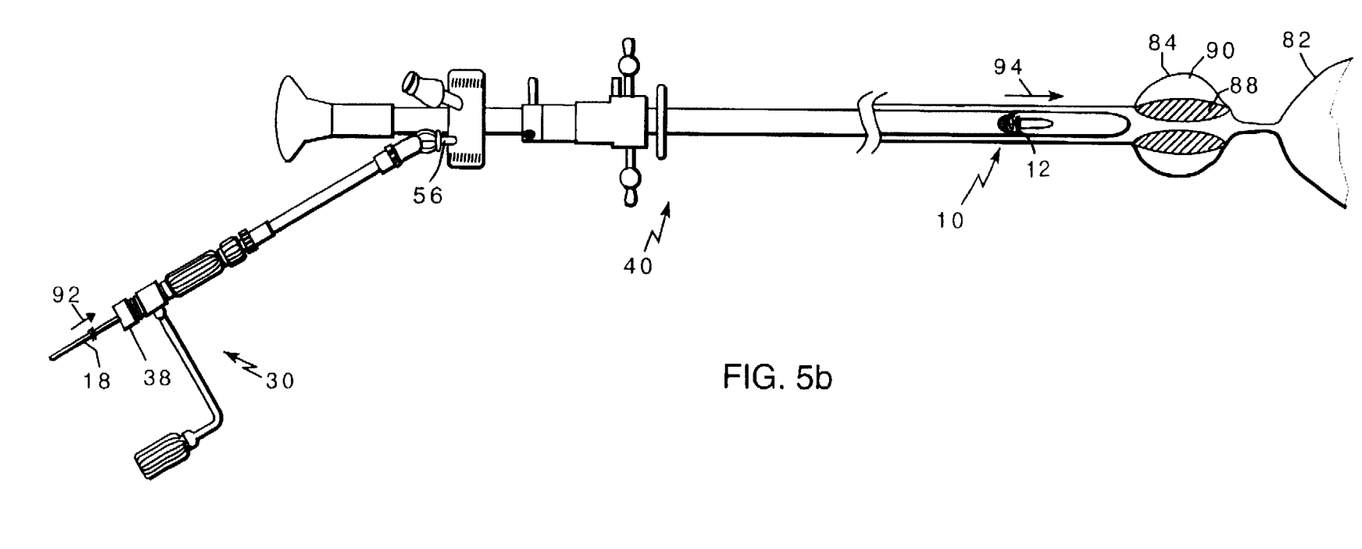

Referring to FIG. 5b, after laser coagulation, laser fiber 86 is removed from cystoscope 40 and replaced with resecting brush 10, through working channel 56. Actuation assembly 30 is then attached to cystoscope 40, as described previously. With tuohy-borst connector 38 in the open position, the proximal end of torque catheter shaft 18 is moved axially in the direction of arrow 92 causing bristles 12 to move in the direction of arrow 94.

Figures 5C, 5D:
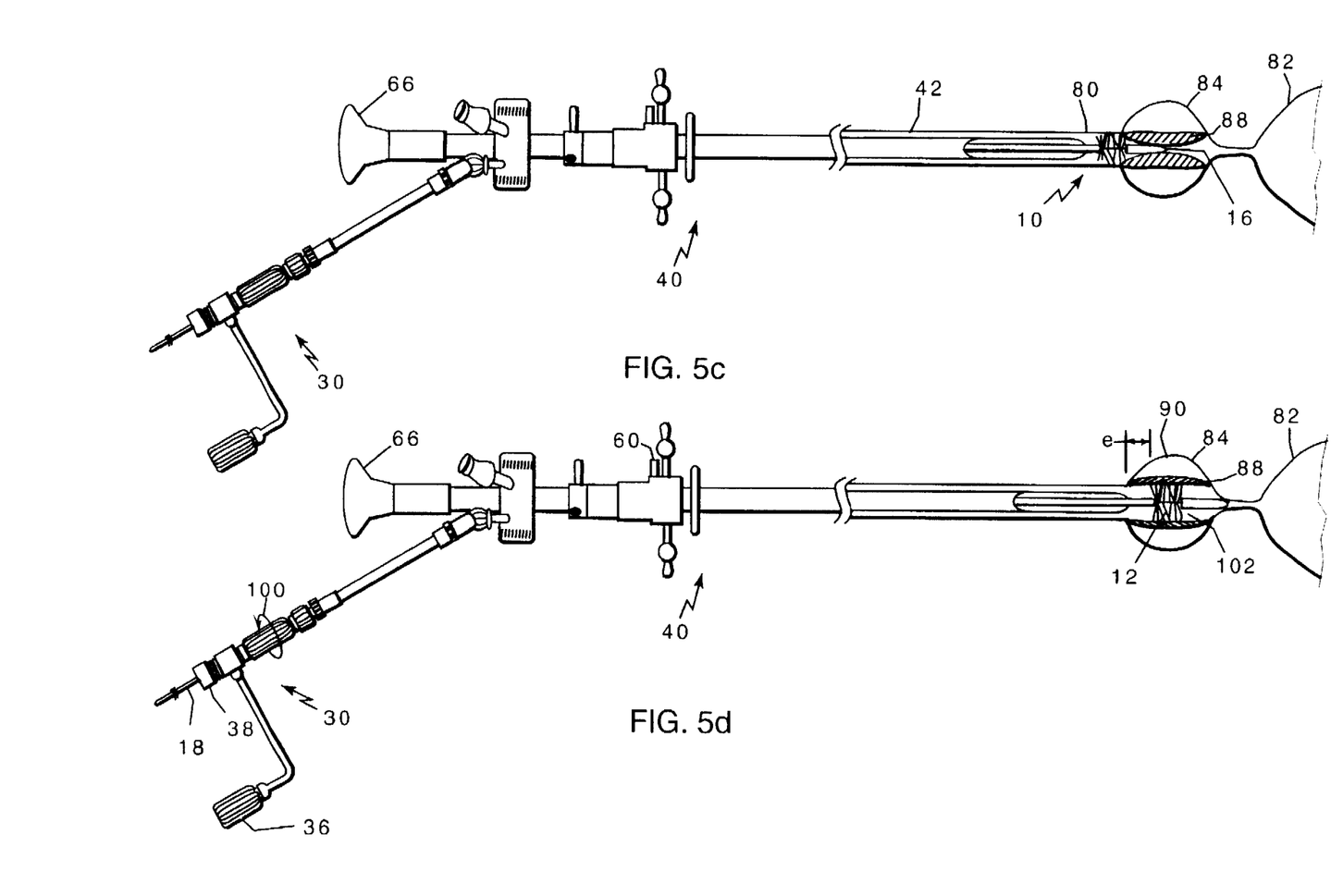

Referring to FIGS. 5c and 5d, atraumatic tip 16 helps to guide the resecting brush 10 into the prostate and into the collapsed urethra 80 without causing trauma. While looking through eyepiece 66, the physician positions bristles 12 at the coagulated adenoma 88 by manipulating torque catheter 18 until a distance "e" of about 1 cm is obtained between the distal end of cystoscope 40 and the proximal end of bristles 42. Tuohy-borst connector 38 is then tightened about torque shaft 18 to maintain the axial position of bristles 12.

To resect the coagulated tissue, the physician rotates crank handle 36 about the centerline 1 of crank assembly 30 which causes swivel fitting 34, tuohy-borst connector 38, and the proximal end of torque catheter shaft 18 to rotate in the direction of arrow 100. (Alternatively, a motor may be used to rotate crank assembly 30.) The rotation of the proximal end of torque catheter 18 causes a torque to be translated through the catheter such that bristles 12 are similarly rotated, as previously discussed. The bristles 12 remove the treated coagulated tissue, or adenoma 88, which is granular and poorly secured to the lumen wall, but does not remove the normal, healthy, untreated tissue that is axially adjacent or beneath the treated tissue. For example, the physician may initially locate the distal end of the brush against the proximal area of coagulated tissue, begin rotation, and then simultaneously move the brush distally as tissue is removed. In this case, the proximal portion of the brush is initially in contact with healthy tissue proximal of the irradiated area but this tissue is not damaged because of the construction and operation of the brush.

The physician continues to rotate crank handle 36 until the desired portion of the laser coagulated adenoma 88 is removed and a cavity 102, that is satisfactory to the physician, is formed. The speed of rotation is typically about 40 rpm and is dependent upon the diameter of bristles 12, the diameter of each bristle, and the diameter of the body lumen. (In an alternative embodiment, the physician may use reciprocal axial motion to remove coagulated adenoma 88.) During this procedure, irrigation, such as, for example, saline solution, is introduced through irrigation port 60 to continuously flush the removed coagulated tissue. Additionally, deflection arm 48 may be used to help position bristles 12 in order to form a sufficient cavity 102. In an alternative embodiment, a resecting brush may have a preset curve at the distal end of torque shaft 18 that offsets the brush radially to facilitate resecting the treated tissue.

Figure 5E:
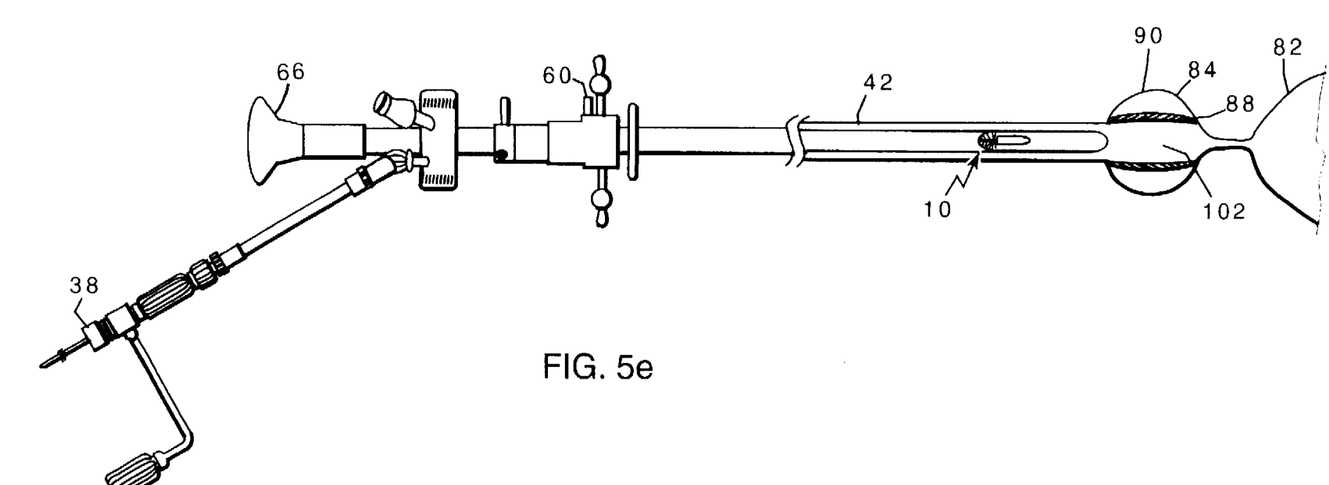

Referring to FIG. 5e, when the desired cavity 102 is achieved, tuohy-borst connector 38 is rotated, so that it is in the open position, and resecting brush 10 is pulled proximally into cystoscope sheath 42. A small layer of coagulated tissue may be left at the prostate as the goal of the brushing procedure is to remove enough of the coagulated tissue to prevent the patient from experiencing urinary retention. The remaining coagulated tissue will naturally slough off during urination.

Other Embodiments

In an alternative embodiment, the resecting brush 10 may be used in a body lumen where the approach to the lumen is appreciably smaller. In this example, the diameter of the bristles may be larger than the sheath of the cystoscope. In this embodiment, the bristles are constrained by a retractable sheath, or by the working channel of the endoscope. When this constraint is removed, the bristles expand to a larger diameter. After use, the bristles collapse axially when pulled back into the constraint. In embodiments, the brush may be constructed for delivery through other catheters, such as an endoscope or, the brush may be constructed for delivery directly through the lumen and positioned using, e.g., radiographic techniques. In further embodiments, the brush may be fixed to the end of an endoscope. In embodiments, the tissue removal action may be a reciprocating axial motion. The brush may be constructed with bristles extending radially along a short arc for selectively resecting only a certain quadrant of the lumen wall.

In embodiments, the apparatus and techniques, according to the invention, may be adapted for use in various body lumens, such as, for example, the colon, the esophagus, the biliary tract, the pancreas, and the bronchial tubes. The invention may be particularly useful in treating esophageal or pulmonary cancers, since healthy tissue beneath the diseased site must be carefully preserved to avoid a puncture, which can have fatal consequences. Additionally, the apparatus and technique may be used to remove an occlusion forming within the apertures of a medical prosthesis, such as a stent that has been previously deployed, to open an occluded area in the above mentioned body lumens.

Additionally, the tissue may be coagulated using cautery or electrical conduction methods, such as, for example, heating elements or heated balloons, or by microwave treatment or chemical injection, such as ethanol treatment, which also destroy intercellular matrices or cell membranes.

In embodiments, other ways can be used to apply sufficient force to resect coagulated tissue, without causing damage to the adjacent healthy tissue, including water jets. In this embodiment, the water jet radially directs a stream of water towards the treated tissue. The velocity and diameter of the stream of water is sufficient to remove the treated tissue without damaging adjacent healthy tissue. The water jet may rotate or be rotated by a physician to ensure that the entire circumferential adenoma is impinged with the water stream.

In embodiments, the resecting brush may be coupled to a coagulating implement. A coagulating implement with a laser fiber is discussed in U.S. Ser. No. 08/062,656, incorporated supra, that can be modified as discussed below to include a resecting element, such as a resecting brush. The devices can be delivered through a delivery catheter, such as an endoscope or a cystoscope, or they may be delivered directly into the lumen.

Figure 6:
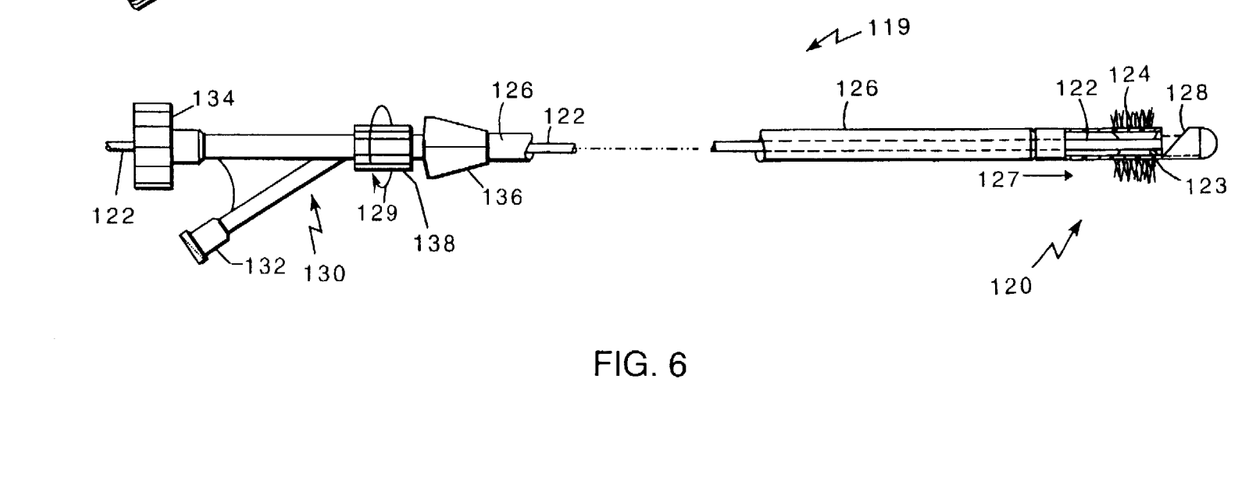
FIGS. 6 to 8 are partial cross-sectional side views of other resecting assemblies.

Referring to FIG. 6, a surgical instrument 119 including a distal end 120 and proximal end 130 is illustrated. The distal end 120 is constructed to direct laser light onto tissue and to resect the tissue after coagulation with a resecting brush 124. The laser light is directed from the end of a optical fiber 122 inside a tip assembly onto a mirror 128, which reflects the light to side onto tissue. The resecting brush 124 extends radially outward from a location proximal to reflecting mirror 128. The proximal end 130 of the surgical instrument 119 is a Y-connector. Laser fiber 122 extends from the proximal end to the distal end. Guide 123 insures proper alignment of laser fiber 122. Proximal end 130 includes a flush connector 132 and a tuohy-borst fitting 134, used for sealing the laser fiber 122 in a feed-through arrangement. A female luer fitting 136 connects the proximal end of catheter 126 to the proximal end 130 of the surgical instrument 119. Catheter 126 has a torque catheter design, i.e., catheter body 126 has a laminate construction of nylon, a braided steel mesh, and an outer layer of nylon to increase its torsional rigidity and provide good flexibility. The fitting 138 is a swivel coupling that allows the catheter, and hence the mirror and brush 124, to be rotated about laser fiber 122 while the laser fiber remains rotationally stationary.

In use, to irradiate a desired portion of tissue, the physician rotates knob 138 (arrow 129). This translates a torque through catheter 126 causing the distal end 120 of the surgical instrument to rotate, including reflecting mirror 128, resulting in a circumferential laser coagulated adenoma (not shown), as discussed previously. After laser coagulation, a physician positions brush 124 at the coagulated adenoma by moving the surgical instrument 119 distally in the direction of arrow 127. Then, knob 138 is rotated again, in the direction of arrow 129, such that resecting brush 124 rotates, removing the treated coagulated tissue. Flushing fluid can be delivered through the flush connector 132 to cool the optical components and/or the tissue during the irradiation step, as well as during the resecting step to flush resected tissue. In another embodiment, the brush is located on a portion of the catheter proximal of the mirror that has smaller outer diameter so that the bristles do not substantially extend radially beyond the distal portions of the device. In this case, the bristles contact the irradiated tissue as it prolapses against the brush when the device is moved distally after laser irradiation. A retractable sheath can also be provided over the brush during laser irradiation; the sheath is retracted to expose the brush to retract the tissue.

In further embodiments, flush flow ports are provided in the catheter at the location of the brush so that flushing fluid can be flowed directly onto the tissue as it is being resected.

Figure 7:
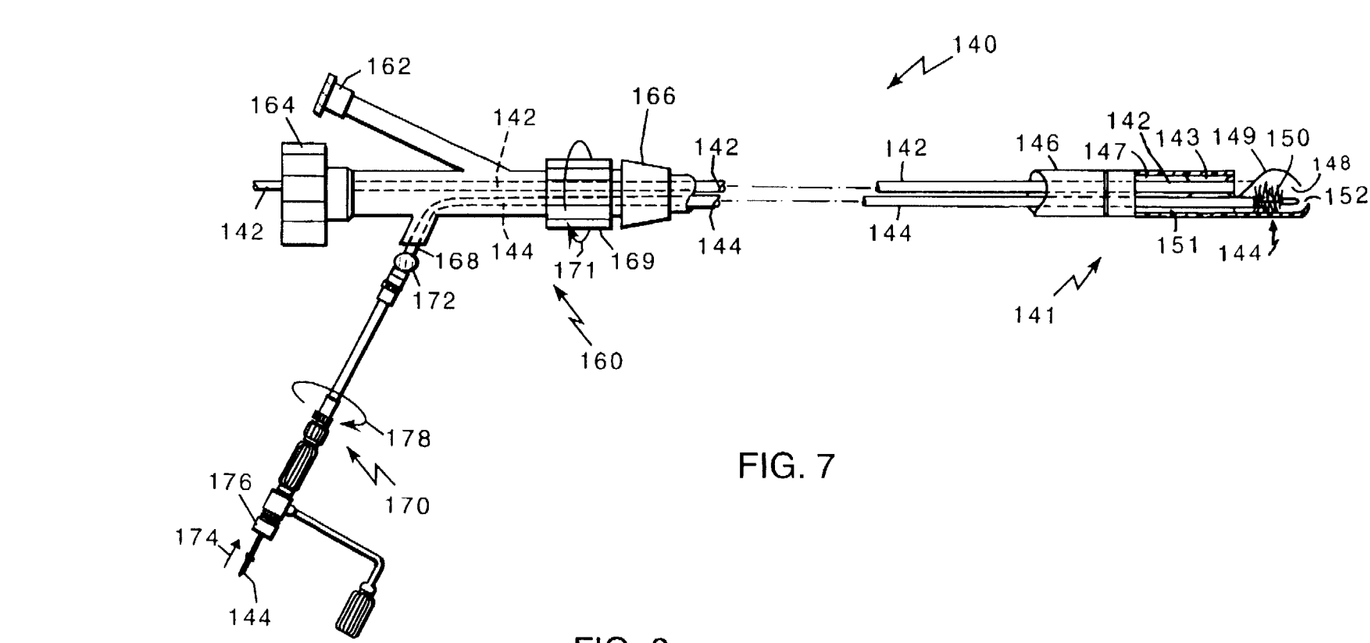

Referring to FIG. 7, in another embodiment, a surgical instrument 140 including a distal end 141 and a proximal end 160 is illustrated. Distal end 141 includes a laser fiber 142 and resecting brush 144 that can be disposed within catheter 146. In this embodiment, laser fiber 142 is eccentric with catheter 146 and resecting brush 144 is concentric with catheter 146. Catheter 146 has cavity 148 that is located distal to reflecting mirror 149 and is sized such that bristles 150 fit within cavity 148. Additionally, catheter 146 has an opening 152 at its distal end. (The opening may be covered by a slotted elastic polymer.) Laser fiber 142 is located inside the surgical instrument and extends from the proximal end to the distal end. Guide 143, which is connected to the inner wall of catheter 146, insures that the laser fiber 142 is properly aligned. Preferably, catheter 146 has two separate lumens. The laser fiber is housed in lumen 147, having the guide at its distal end to insure proper alignment to the mirror 149. The second lumen 151 houses the torque catheter-portion of resecting brush. A female luer fitting 166 connects the proximal end of catheter 146 to a swivel coupling 169 at the proximal end 160 of the surgical instrument 140. Catheter 146 has a torque catheter design, i.e., catheter body 146 has a laminate construction of nylon, a braided steel mesh, and an outer layer of nylon to increase its torsional rigidity and provide good flexibility.

Proximal end 160 also includes a flush connector 162 and a tuohy-borst fitting 164 which is used for sealing the laser fiber 142 in a feed-through arrangement. The torque catheter portion of resecting brush 144 extends through port 168. A crank actuation assembly 170, constructed as discussed above, is connected to proximal end 160 of surgical instrument 140 by, for example, ball fitting 172, at port 168.

In use, to irradiate the tissue to be treated, the physician rotates knob 169 in the direction of arrow 171. This translates a torque through catheter 146 causing the distal end 141 of the surgical instrument to rotate, including reflecting mirror 149, resulting in a circumferential laser coagulated adenoma (not shown), as discussed previously. The construction of the surgical instrument permits such rotation without rotating laser fiber 142. After laser coagulation, the physician positions the distal end 141 of the device proximally of the coagulated tissue and positions resecting brush 144 at the coagulated tissue by moving brush 144 distally, in the direction of arrow 174, such that it exits catheter 146 through opening 152. As previously described, tuohy-borst 176 of the actuation assembly 170 is tightened about brush 144 to maintain its axial position. Then, the physician rotates actuation assembly 170 in the direction of arrow 178 such that resecting brush 144 removes the treated coagulated tissue. Fluid may flow through both lumens.

Figure 8:
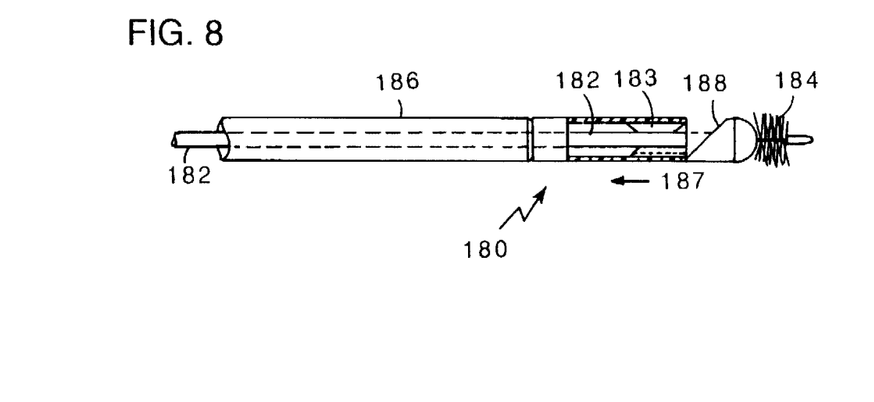

Referring to FIG. 8, in another embodiment, a distal end 180 of a surgical instrument is illustrated. Distal end 180 includes a laser fiber 182 and a resecting brush 184. Laser fiber 182 is disposed within catheter 186. Guide 183 insures that laser fiber 182 is properly aligned with reflecting mirror 188. Resecting brush 184 is attached to the distal end of catheter 186 by, for example, welding. Resecting brush 184 includes atraumatic guiding tip 190. Catheter 186 has a torque catheter design, i.e., catheter body 186 has a laminate construction of nylon, a braided steel mesh, and an outer layer of nylon to increase its torsional rigidity and provide good flexibility. Referring back to FIG. 6, the surgical instrument would include proximal end 130, as previously described.

Referring to FIG. 6 and 8, in use, to irradiate the tissue to be treated, a physician rotates knob 138 in the direction of arrow 129. This translates a torque through the catheter, causing the distal end 180 of the surgical instrument to rotate, including reflecting mirror 188, resulting in a circumferential laser coagulated adenoma (not shown), as discussed previously. After laser coagulation, a physician positions brush 184 at the coagulated adenoma by moving the surgical instrument proximally in the direction of arrow 187. Then, knob 138 is rotated again, in the direction of arrow 129, such that resecting brush 184 rotates, removing the treated coagulated tissue.

Still other embodiments are in the following claims.

What is claimed is:

1. A method for treating an occluded body lumen, comprising:

advancing a tissue coagulating implement into a body lumen, positioning said coagulating implement at an occluded site within said body lumen, coagulating bodily matter at said occluded site using said coagulating implement, providing a resecting implement, said resecting implement including an elongated catheter having a proximal and a distal end and a brush formation located near said distal end, said brush formation including a bristle structure of selected stiffness to apply a force within said body lumen that is sufficient to resect coagulated bodily matter but insufficient to resect non-coagulated bodily matter, positioning said brush formation at said occluded site and actuating said brush formation whereby said bristle structure resects and removes said coagulated bodily matter without substantially damaging adjacent non-coagulated bodily matter, and removing said coagulating implement and said resecting brush from said patient.

2. A method for treating an occluded body lumen, comprising:

advancing a tissue coagulating implement into a body lumen, positioning said coagulating implement at an occluded site within said body lumen, coagulating bodily matter at said occluded site using said coagulating implement, providing a resecting implement constructed to apply a force within said body lumen that is sufficient to resect coagulated bodily matter but insufficient to resect non-coagulated bodily matter, positioning said resecting implement at said occluded site and actuating said resecting implement at said occluded site to apply said force against said occluded site, whereby said resecting implement removes said coagulated bodily matter but avoids substantially damaging adjacent non-coagulated bodily matter when said resecting implement is actuated against and applies said force against said non-coagulated bodily matter, and removing said coagulating implement and said resecting implement from said patient.

3. The method of claim 2 including:

prior to advancing said tissue coagulating implement into said body lumen, inserting a delivery catheter into said body lumen through which said tissue coagulating implement and said resecting implement are inserted.

4. The method of claim 2, wherein said step of positioning said coagulating implement comprises positioning said coagulating implement at an occluded site within the prostate to treat benign prostate hyperplasia.

5. The method of claim 2, wherein said step of coagulating said bodily matter comprises coagulating said bodily matter using a heating implement.

6. The method of claim 5, wherein said step of coagulating said bodily matter using a heating implement comprises coagulating said bodily matter using a laser transmission apparatus.

7. The method of claim 2 further comprising:

flushing said body lumen after said positioning and actuating steps.

8. The method of claim 2, wherein said actuating step comprises rotating said resecting implement to resect and remove said coagulated bodily matter in a circumferential pattern within said lumen.

9. A surgical resecting brush assembly, comprising:

an elongated catheter having a proximal and a distal end and being sized and constructed for delivery through a body lumen to a site that is occluded with body matter that has been effected by heat treatment, and a brush formation near said distal end of said elongated catheter, said brush formation including a bristle structure means of sufficient stiffness for resecting and removing said effected bodily matter when said brush formation is actuated relative to said occluded site to apply a force against said occluded site, and for avoiding substantial damage to adjacent, healthy tissue when said brush formation is actuated against and applies said force against said healthy tissue.

10. The brush assembly of claim 9 including an atraumatic guiding tip located at said distal end of said elongated catheter.

11. The brush assembly of claim 9 wherein said elongated catheter includes a stainless steel mesh layer surrounded by at least one polymer layer for torque-transmission so that said brush formation near said distal end of said elongated catheter can be rotated by torque application at said proximal end of said elongated catheter.

12. The brush assembly of claim 9 wherein said elongated catheter includes a wire coil so that said elongated catheter can be delivered through said body lumen by application of axially compressive forces to said proximal end of said catheter.

13. The brush assembly of claim 9 wherein said elongated catheter includes a biocompatible polymeric outer coating.

14. The brush assembly of claim 9 wherein said brush formation includes bristle structure means having a stiffness of about 1500N/mm$^2$.

15. The brush assembly of claim 9 wherein said bristle structure means comprises bristles extend radially from said elongated catheter.

16. The brush assembly of claim 9 wherein said brush formation has a diameter which corresponds, substantially, to a diameter of said body lumen in a healthy, non-occluded condition.

17. The brush assembly of claim 9 wherein said brush formation has a length which corresponds substantially to a length of said occluded site.

18. The brush assembly of claim 9 further including coupling structure for coupling said brush assembly to a delivery catheter.

19. The brush assembly of claim 18 further including a crank assembly constructed to couple to said coupling structure and to attach to said elongated catheter to actuate said brush formation from outside the body while said brush formation is positioned through said delivery catheter inside the body.

20. The brush assembly of claim 19 wherein said crank assembly and said coupling structure are connected through a swivel coupling.

21. The brush assembly of claim 19 wherein said elongated catheter is releasably connected to said crank assembly by a compression fitting.

22. A surgical kit for treating occluded body lumens, comprising:

a tissue coagulating implement for coagulating bodily matter at a selected site, and a resecting implement means, having an elongated instrument body deliverable through a body lumen, for applying force within said body lumen that is sufficient to resect and remove coagulated bodily matter when said force is applied to said matter but avoids substantial damage to adjacent non-coagulated tissue when said force is applied against said non-coagulated bodily matter.

23. The kit of claim 22 wherein said resecting implement means includes a brush formation with a bristle structure means of selected stiffness for applying a force within said body lumen sufficient to resect coagulated bodily matter but insufficient to resect non-coagulated bodily matter.

24. The kit of claim 22 wherein said tissue coagulating implement and resecting implement means are coupled for simultaneous delivery into said lumen.

25. The kit of claim 24 wherein said coagulating implement includes an elongated member and said resecting implement means is attached to said member.

26. The kit of claim 25 wherein said resecting implement means is attached to the distal end of said member.

27. The kit of claim 25 wherein said resecting element means is attached along the length of said member.

* * * * *